(12) United States Patent
Hotter Corripio et al.

(10) Patent No.: US 10,724,004 B2
(45) Date of Patent: Jul. 28, 2020

(54) CELL THERAPY WITH POLARIZED MACROPHAGES FOR TISSUE REGENERATION

(71) Applicant: XCELL MEDICAL SOLUTIONS, S.L., Madrid (ES)

(72) Inventors: María Georgina Hotter Corripio, Barcelona (ES); Ana Maria Sola Martínez, Barcelona (ES); Jorge Vicente Martín Cordero, A Coruña (ES); Pablo García De La Riva Mestre, Madrid (ES); Rubén Domínguez Sánchez, Valencia (ES); Jaime Sánchez Moreno, Valencia (ES); Xavier Ginesta Buch, Madrid (ES); Anna Rodríguez García, Tarrega (ES); Adrián Castillo García, La Rioja (ES)

(73) Assignee: XCELL MEDICAL SOLUTIONS, S.L., Madrid (ES)

( * ) Notice: Subject to any disclaimer, the term of this patent is extended or adjusted under 35 U.S.C. 154(b) by 71 days.

(21) Appl. No.: 15/715,036

(22) Filed: Sep. 25, 2017

(65) Prior Publication Data
US 2018/0087031 A1 Mar. 29, 2018

(30) Foreign Application Priority Data
Sep. 23, 2016 (EP) ..................................... 16382443

(51) Int. Cl.
| | | |
|---|---|---|
| *A61K 35/15* | (2015.01) | |
| *C12M 1/00* | (2006.01) | |
| *C12M 1/04* | (2006.01) | |
| *C12N 5/0786* | (2010.01) | |

(52) U.S. Cl.
CPC ............ *C12N 5/0645* (2013.01); *A61K 35/15* (2013.01); *C12M 1/005* (2013.01); *C12M 1/045* (2013.01); *C12N 2500/02* (2013.01); *C12N 2506/115* (2013.01)

(58) Field of Classification Search
CPC .............. C12N 5/0645; C12N 2500/02; C12N 2506/115; A61K 35/15; C12M 1/045
See application file for complete search history.

(56) References Cited

U.S. PATENT DOCUMENTS

| | | |
|---|---|---|
| 3,886,047 A | 5/1975 | Billups, Jr. |
| 7,976,796 B1 | 7/2011 | Smith et al. |
| 2003/0092178 A1 | 5/2003 | Yerden |
| 2013/0184745 A1 | 7/2013 | Leschinsky |
| 2016/0015884 A1 | 1/2016 | O'Connell, Jr. |
| 2016/0235965 A1 | 8/2016 | Burr |
| 2016/0317864 A1 | 11/2016 | Sato |

FOREIGN PATENT DOCUMENTS

| | | |
|---|---|---|
| ES | 1059764 | 6/2005 |
| GB | 2499372 | 8/2013 |
| WO | WO-2010058898 | 5/2010 |

OTHER PUBLICATIONS

Tripathi et al., Oncotarget, Jun. 2014, vol. 5, No. 14, p. 5350-5368.*
Mantovani et al., TRENDS in Immunology 2002, vol. 23, No. 11, p. 549-555.*
Jung et al., Molecular and Cellular Biology, 2012, vol. 32, No. 19, p. 3938-3948.*
Extended European Search Report dated Mar. 22, 2017, EP Application No. 16382443.6.
Almendros, Isaac et al., "Intermittent Hypoxia-induced Changes in Tumor-associated Macrophages and Tumor Malignancy in a Mouse Model of Sleep Apnea", American Journal of Respiratory and Critical Care Medicine, vol. 189, No. 5, Mar. 1, 2014, 593-601.
Barakat, Rawan et al., "Differential cytokine expression by brain microglia/macrophages in primary culture after oxygen glucose deprivation and their protective effects on astrocytes during anoxia", Fluids and Barriers of the CNS, 12:6, 2015, 1-10.
Escribese, María M., "Influence of low oxygen tensions on macrophage polarization", Immunobiology 217, 2012, 1233-1240.
Ferrante, Christopher J. et al., "Regulation of Macrophage Polarization and Wound Healing", Advances in Wound Care, vol. 1, No. 1, 2012, 10-16.
Hunt, Thomas K. et al., "Studies on inflammation and wound healing: Angiogenesis and collagen synthesis stimulated in vivo by resident and activated wound macrophages", Surgery, vol. 96, No. 1, Jul. 1984, 48-54.
Kigerl, Kristina A. et al., "Identification of Two Distinct Macrophage Subsets with Divergent Effects Causing either Neurotoxicity or Regeneration in the Injured Mouse Spinal Cord", The Journal of Neuroscience vol. 29, No. 43, Oct. 28, 2009, 13435-13444.
Lewis, J. S., "Macrophage responses to hypoxia: relevance to disease mechanisms", Journal of Leukocyte Biology, vol. 66, Dec. 1999, 889-900.
Martinez, Fernando O. et al., "Alternative Activation of Macrophages: An Immunologic Functional Perspective", Annual Review of Immunology, vol. 27, Dec. 15, 2008, 451-483.

(Continued)

*Primary Examiner* — Kade Ariani
(74) *Attorney, Agent, or Firm* — Womble Bond Dickinson (US) LLP

(57) ABSTRACT

The invention provides an in vitro method for inducing macrophage polarization to an M2 phenotype. The method comprises the in vitro exposure of macrophages to repeated series of hypoxia-reoxygenation. Activated M2 macrophages obtained by this method overexpress molecules important for tissue remodeling and amelioration of inflammation, thus they are useful as cell therapy for tissue regeneration. The invention also provides pharmaceutical compositions and kits comprising the M2 macrophages obtained by the method, as well as a device for inducing hypoxia and re-oxygenation conditions on isolated macrophages according to the method.

5 Claims, 10 Drawing Sheets

(56) References Cited

OTHER PUBLICATIONS

Martinez, Fernando Oneissi et al., "Macrophage activation and polarization", Frontiers in Bioscience 13, Jan. 1, 2008, 453-461.
McCourtie, Anton S. et al., "Alveolar Macrophage Secretory Products Effect Type 2 Pneumocytes Undergoing Hypoxia-Reoxygenation", The Annals of Thoracic Surgery, vol. 86, 2008, 1774-1780.
Michiels, Carine et al., "Cycling hypoxia: A key feature of the tumor microenvironment", Biochimica et Biophysica Acta 1866, 2016, 76-86.

* cited by examiner ized to an M2 phenotype which are suitable for tissue regeneration. It also refers to the M2 macrophage populations obtained by this method and to medicaments and pharmaceutical compositions comprising the same for their use in cell therapy in the regeneration of damaged, injured or impaired tissue.

CELL THERAPY WITH POLARIZED MACROPHAGES FOR TISSUE REGENERATION

CROSS-REFERENCE TO RELATED APPLICATION

The present patent application claims priority to European Patent Application No. 16382443.6, filed Sep. 23, 2016, the disclosure of which is incorporated herein by reference.

This invention belongs to the field of cell therapies for tissue repair. Specifically, it refers to an in vitro method for obtaining macrophages polarized to an M2 phenotype which are suitable for tissue regeneration. It also refers to the M2 macrophage populations obtained by this method and to medicaments and pharmaceutical compositions comprising the same for their use in cell therapy in the regeneration of damaged, injured or impaired tissue.

BACKGROUND ART

Macrophages are derived from circulating monocytes that exit the vasculature and invade into the surrounding tissues where they differentiate under the influence of local signals into resident tissue macrophages. Resident macrophages have a variety of roles; they patrol tissues for damaged or apoptotic cells, which they clear by phagocytosis, they identify and eliminate such invading pathogens as bacteria, fungi, and virally infected cells, they scavenge lipoproteins, and they are also responsible for regulating tissue oxygenation by influencing the formation of new blood vessels and modulating vascular permeability.

Macrophages are a highly versatile cell type with an impressive repertoire of functions depending on their location and activation status. This includes antigen presentation, anti-bacterial and antitumor activity, and the secretion of a wide variety of regulatory peptide factors, prostanoids, and enzymes.

Macrophages are therefore a population of immune cells that orchestrate a diverse array of functions including inflammation, tissue repair, and immune responses. This functional diversity is achieved by the remarkable heterogeneity of macrophages, which have the capacity to dramatically change their phenotype as a result of differentiated plasticity as well as local environmental cues.

As immune effector cells, the role of macrophages in inflammation and host defense is well characterized. Additionally, macrophages are integral in the promotion of proper wound healing as well as the resolution of inflammation in response to pathogenic challenge or tissue damage (Christopher J. Ferrante and Samuel Joseph Leibovich, 2012, Advances in wound care, 1: 1, 10-16). These diverse physiological functions stem from the remarkable plasticity of macrophages, which allows these cells to dramatically change their form and function in response to local environmental signals. Unstimulated macrophages are typically quiescent; stimulation of these cells, however, results in the development of markedly polarized phenotypes in response to molecular cues residing in the local microenvironment.

Current classification of macrophages recognizes polarization into two distinct phenotypes. Thus, macrophages are generally classified as either classically (M1) or alternatively (M2) activated. M1 macrophages have a proinflammatory phenotype exhibiting increased phagocytic activity and secretion of proinflammatory cytokines that aid in the removal of pathogens and abnormal or damaged tissues. M2 macrophages have a polar opposite phenotype exhibiting high levels of anti-inflammatory cytokines and fibrogenic and angiogenic factors that serve to resolve inflammation and promote wound healing (Martinez F O, Helming L, and Gordon S. 2009. Annu Rev Immunol; 27: 451-483). Both M1 and M2 macrophages express distinct molecular markers.

M1 macrophages are induced by recognition of pathogen-associated molecular patterns, such as bacterial lipopolysaccharides (LPS) and peptidoglycan, or damage-associated molecular patterns, such as released intracellular proteins and nucleic acids, as well as stimulation by the T-cell-secreted cytokine interferon gamma (IFN-γ). M1 represent a proinflammatory phenotype, exhibiting increased phagocytic and antigen processing activity as well as increased production of proinflammatory cytokines (e.g., interleukin 1 [IL-1], IL-6, IL-12, and tumor necrosis factor alpha [TNF-α]) and oxidative metabolites (e.g., nitric oxide and superoxide) to promote host defense and removal of damaged tissue. In contrast, M2 macrophages are induced by a variety of stimuli (e.g., IL-4/IL-13, glucocorticoids) and represent a phenotype that is potentially important in the promotion of wound healing and tissue remodeling as well as the resolution of inflammation (Martinez F O, Sica A, Mantovani A, and Locati M. 2008. Front Biosci; 13: 453-461).

The remarkable plasticity of macrophages has important implications for clinical science. Proper macrophage polarization is necessary in several important physiological processes including, but not limited to, wound healing, immune response, and nerve/muscle regeneration (Kigerl K A, et al., 2009, J Neurosci; 29: 13435-13444). Thus, it is not surprising that aberrations in macrophage polarization are associated with some of the pathology observed in defective wound healing, diabetes, muscular dystrophy, fibroproliferative diseases such as rheumatoid arthritis and liver and lung fibrosis, as well as tumor progression. Elucidating the specific microenvironmental signals that contribute to macrophage polarization could potentially lead to methods for the pharmacological manipulation of macrophage phenotypes to promote favorable processes (e.g., wound healing) or inhibit pathologic processes (e.g., fibroproliferative diseases and tumor growth).

As mentioned before, the ability of macrophages to alter their phenotype in response to different environmental stimuli has led to considerable research to both identify the wide variety of signals that induce these phenotypes as well as characterize the molecular profiles of M1 and M2 macrophages. However, macrophage polarization is a complex process and it has emerged that there is a broad set of signals that induce distinct macrophage phenotypes.

Of the increased numbers of macrophages present in diseased tissues, many are seen to accumulate in or adjacent to poorly vascularized, hypoxic sites, where considerable tissue damage may have occurred. High macrophage numbers have been reported in avascular and necrotic sites in breast and ovarian carcinomas, hypoxic areas of dermal wounds (Hunt, T. K., et al., 1983, Surgery, 96, 48-54), avascular locations of atherosclerotic plaques, the synovium in joints with rheumatoid arthritis, ischemic sites in proliferative retinopathy, and around vascular occlusions in cerebral malaria.

Macrophages are able to function under such adverse conditions by altering gene expression and adapting their metabolic activity. Hypoxia can induce marked changes in the secretory activity of macrophages, eliciting the release of both pro-angiogenic and inflammatory cytokines by macrophages in vitro and in vivo. Some studies have reviewed the effects of experimental hypoxia on various macrophage functions (Claire Lewis, et al., 1999, Journal of Leukocyte Biology, 66, 889-900; Maria M Escribese, et al., 2012, Immunobiology, 217, 1233-1240).

However, as hypoxia is usually transient in diseased tissues, and rarely, if ever, acts on cells in isolation from other pathogenic stimuli, these studies have highlighted the requirement of co-stimuli for its effects on macrophages.

On the other hand, methods based on physiotherapy for treating musculoskeletal injuries, including injuries to muscle, tendon and fascial components, immobilization, and various physiotherapies, have limited success. The use of drugs to reduce the pain is also commonly used, but none of these methods have been able to accelerate the healing process and reduce scar formation. The use of platelet rich plasma and stem cells seems to be a promising method for the treatment of these injuries, and several approaches has been developed, but none of these methods has achieved a complete regeneration of the injured tissue. Furthermore, the use of stem cell therapy has intrinsic risks given the loss of control on the administered cells once they have been implanted in the recipient with potential tumorigenic risk or inappropriate differentiation. Thus, improved methods of treating injured tissues in patients are required.

Ischemia preconditioning has been commonly used to prevent ischemia reperfusion injures. US2013184745, for example, describes a device of ischemic preconditioning. Several patent documents describe the use of blood flow restriction in muscle training (for instance, US2016235965 and US2016317864). But the effect of this technique has not been previously used in treatment of musculoskeletal injuries in order to accelerate the wound healing and tissue regeneration, reducing scar formation.

From the state of the art a plurality of medical devices for inducing hypoxia in cell culture are known. For example, in GB2499372 it is described a hypoxic pressure chamber for cell culture that comprises a plastic chamber with a gas inlet and a gas outlet. In U.S. Pat. No. 3,886,047 it is disclosed a hypoxic chamber with inlet and outlet gas tubes for culture growth under controlled atmosphere.

It is also known a culture chamber, which is described in US2003092178, where oxygen concentration is monitored to control the gas profile inside the chamber. Additionally, document WO2010058898 proposes a device comprising a culture chamber for cell culture, a vacuum pump for discharging air from the culture chamber to the outside, an automatic control valve for controlling a supply pipe of a carbon dioxide tank for supplying carbon dioxide into the culture chamber and a supply pipe of a nitrogen tank for supplying nitrogen into the culture chamber.

All these devices have in common that have been designed to culture cells on a hypoxic chamber and are useful for investigational purposes. None of these devices would be useful for clinical application since the processes are not carried out in aseptic conditions. In all the systems previously described, the cell cultures are placed and removed from the hypoxic chamber to external environment, and therefore can be easily contaminated.

On the other hand, several systems have been designed to separate and concentrate blood components from a blood sample. Some examples are patents ES1059764, U.S. Pat. No. 7,976,796 and US2016015884 but there are not systems described to induce hypoxia on the cells contained in these devices.

In summary, methods for obtaining macrophages polarized to a phenotype that promotes wound healing and, in general, tissue regeneration, are required. Specifically, methods for the artificial polarization of macrophages into an M2 phenotype would be of special interest, as M2 macrophages present a phenotype that is important in the promotion of wound healing and tissue remodeling as well as in the resolution of inflammation. The development of these methods would therefore enable the artificial manipulation of macrophage polarization to obtain macrophages phenotypes which enhance normal physiological processes, such as wound repair.

DESCRIPTION OF THE INVENTION

The present invention provides an in vitro method for inducing macrophage polarization (differentiation) to an M2 phenotype useful for tissue repair. Activated M2 macrophages obtained by this method overexpress molecules important for tissue remodeling and amelioration of inflammation, such as NGAL and anti-inflammatory cytokines (IL-10). Thus, M2 macrophages obtained by this method are useful as cell therapy for tissue regeneration.

The method described in the present invention comprises the in vitro or ex vivo exposure of isolated macrophages, preferably in culture, more preferably which have been previously isolated from the patient, to repeated and consecutive series of hypoxia-reoxygenation (each serie consisting of a first step under hypoxia conditions followed by a second step under reoxygenation conditions). More preferably, this method consists of 3 or 4 series of hypoxia-reoxygenation, even more preferably the method consists of 4 series of hypoxia-reoxygenation. Macrophages cultured under these conditions acquire, as a result of the hypoxia-reoxygenation periods, an activated M2 phenotype. Thus, these resultant macrophages are useful for their subsequent administration to the patient in the damaged tissue wherein they promote complete tissue regeneration.

Examples below show that those polarized M2 macrophages obtained by the method of the invention overexpress, at least, NGAL and preferably also IL-10 (more preferably at mRNA level) compared to cultured macrophages which have not been subjected to the hypoxia-reoxygenation protocol described in this invention (control). Furthermore, this NGAL overexpression is not observed in macrophages subjected to a different number of hypoxia-reoxygenation series than those proposed in the present invention. For instance, examples below show that those macrophages that have been subjected to 5 hypoxia-reoxygenation series do not show an increase in NGAL expression compared to the control (macrophages non-subjected to hypoxia-reoxygenation conditions). These results prove that the exposure to the specific number of hypoxia-reoxygenation series indicated in the method described herein is advantageous over other different number of series. Thus, the method described in the present invention provides advantageous M2 activated macrophages which cannot be obtained by other induction protocols, even those also involving the culture under hypoxic conditions.

M2 macrophages obtained by the method described in the present invention may be therefore used in cell therapy methods for tissue regeneration through their administration to the injured area of the subject in need thereof. Preferably, these M2 macrophages may be injected, more preferably via intramuscular, in the damaged area for tissue regeneration, even more preferably for muscle repair.

One of the main advantages of this invention is that the macrophages to be cultured for polarization under the conditions described in the method of the invention may be autologous. This reduces or removes those risks associated to adverse immunological reactions in the patient to be administered with the polarized cells. Moreover, macrophages to be cultured under the conditions described in the method of the invention may be easily obtained and isolated from the patient, preferably from the bloodstream. Additionally, the resultant M2 macrophages are capable of promoting tissue regeneration, inflammation reduction and scar or fibrosis clearance (fibrosis reduction).

Therefore, an aspect of the present invention refers to a method for obtaining macrophages polarized or differentiated to an M2 phenotype, hereinafter "the method of the invention", that comprises:

a. subjecting isolated macrophages to at least one but less than five series of hypoxia-reoxygenation, and b. recovering the macrophages obtained after step (a).

This method of the invention may be also described as "a method for macrophage polarization/differentiation to an M2 phenotype", or "a method for obtaining macrophages with an M2 phenotype", or "a method for obtaining activated macrophages with a phenotype that induces tissue remodelling, regeneration or repair".

Macrophages in step (a) of this method of the invention may be in an in vitro cell culture or, preferably, may be isolated in capsules which comprise external control of oxygen tension.

In a preferred embodiment of the method of the invention, the macrophages of step (a) are human or non-human mammal macrophages, more preferably they are human macrophages. In an even more preferred embodiment, the macrophages are autologous. The term "autologous" refers to macrophages that have been obtained from the same individual as that who will be administered with the resultant M2 macrophages. Thus, the term "autologous" involves one (the same) individual as both donor and recipient.

"Macrophages" are a type of white blood cell and are within immune cells that orchestrate a diverse array of functions including inflammation, tissue repair, and immune responses. For instance, they engulf and digest cellular debris, foreign substances, microbes, cancer cells, and anything else that does not have the types of proteins specific of healthy body cells on its surface in a process of phagocytosis. Macrophages are found in essentially all tissues, where they patrol for potential pathogens by amoeboid movement. They take various forms (with various names) throughout the body (e.g., histiocytes, Kupffer cells, alveolar macrophages, microglia, and others), but all are part of the mononuclear phagocyte system. Besides phagocytosis, they play a critical role in nonspecific defense (innate immunity) and also help initiating specific defense mechanisms (adaptive immunity) by recruiting other immune cells such as lymphocytes. For example, they are important as antigen presenters to T cells. Beyond increasing inflammation and stimulating the immune system, macrophages also play an important anti-inflammatory role and can decrease immune reactions through the release of cytokines. Macrophages can be identified, for example but without limitations, using flow cytometry or immunohistochemical staining by their specific expression of proteins such as, but without limitation, CD14, CD40, CD11 b, CD64, F4/80 (mice)/EMR1 (human), lysozme M, MAC-1/MAC-3 and/or CD68.

The macrophages of step (a) of the method of the invention may be also monocytes or M1 macrophages. Thus, the term "macrophages" as used in step (a) of the method of the invention includes those macrophages produced by the differentiation of monocytes, macrophages of any differentiated or undifferentiated phenotype (including M1 macrophages) and any cell encompassed within the mononuclear phagocyte system, including monocytes. Thus, the term "macrophage" as use in step (a) of the method of the invention refers to "cells of the mononuclear phagocyte system". Likewise, the term "macrophage" as used in step (a) of the method of the invention includes, but without limitation, adipose tissue macrophages, monocytes, Kupffer cells, sinus histiocytes, alveolar macrophages (dust cells), tissue macrophages (histiocytes) leading to giant cells, Langerhans cells, microglia, Hofbauer cells, intraglomerular mesangial cells, osteoclasts, epithelioid cells, red pulp macrophages (sinusoidal lining cells), peritoneal macrophages, LysoMac and the like. In a preferred embodiment, the macrophages of step (a) are peritoneal macrophages. In another preferred embodiment, the macrophages of step (a) are monocytes more preferably previously isolated from the bloodstream of the individual to be treated.

Macrophages may be isolated from an individual, preferably from the bloodstream, before step (a) by any mean known by those skilled in the art for obtaining biological samples comprising the desired cells, in this specific case macrophages or monocytes. Macrophages may be also isolated, not only from bloodstream, but also from any tissue (tissue resident macrophages). Macrophages are preferably isolated by intraperitoneal injection with thioglycolate. Likewise, macrophages may be cultured in step (a) of the method of the invention by any mean and in the presence of any culture medium and support of those known by the skilled in the art that are suitable for the in vitro maintenance and growth of cells, preferably macrophages, more preferably monocytes, even more preferably human monocytes. In a preferred embodiment, macrophages are cultured in step (a) of the method in the presence of RPMI medium supplemented with fetal bovine serum (FBS).

Macrophages can be phenotypically polarized by the microenvironment to mount specific functional programs. Polarized macrophages can be broadly classified in two main groups: classically activated macrophages (or M1) and alternatively activated macrophages (or M2).

Macrophages that encourage inflammation are called "M1 macrophages", whereas those that decrease inflammation and encourage tissue repair are called "M2 macrophages". This difference is reflected in their metabolism; M1 macrophages have the unique ability to metabolize arginine to the "killer" molecule nitric oxide, whereas M2 macrophages have the unique ability to metabolize arginine to the "repair" molecule ornithine. M1 macrophages (previously referred to as "classically activated macrophages") are activated by LPS and IFN-gamma, and secrete high levels of IL-12 and low levels of IL-10. In contrast, the M2 "repair" designation (also referred to as "alternatively activated macrophages") broadly refers to macrophages that function in constructive processes like wound healing and tissue repair, and those that turn off damaging immune system activation by producing anti-inflammatory cytokines like IL-10. M2 is the phenotype of resident tissue macrophages, and can be further elevated by different stimuli such as IL-4, IL-13, immune complex plus toll-like receptor (TLR) or IL-1 receptor ligands, IL10 and glucocorticoids. M2 macrophages produce high levels of IL-10, TGF-beta and low levels of IL-12. Tumor-associated macrophages are mainly of the M2 phenotype, and seem to actively promote tumor growth. M2 macrophages are connected with Th2 immune response. They are important for encapsulation of parasites but they are also responsible for the type H hypersensitivity. Antigen presentation is upregulated (MHC II, CD86). They also contribute on production of extracellular matrix components and tissue remodeling. Glucocorticoids influence the adherence, dissemination, apoptosis and phagocytosis of macrophages.

"Macrophage polarization" is the process wherein macrophage expresses different functional programs in response to microenvironmental signals. There are lots of functional states of macrophage polarization and they can be fully polarized and acquire specific phenotypes like M1 or M2. These specific phenotypes depend on the tissue and specific microenvironment where macrophages are. On one hand, macrophage polarization is very important for host defense against pathogen, but on the other hand it is essential for maintenance of homeostasis, Prolonged M1 type of macrophages is harmful for the organism and that is why tissue repair and restoration is necessary. M2 macrophages are responsible for that tissue repair, although they are also connected with chronic infectious diseases.

A coordinate action of various inflammatory modulators, signaling molecules, and transcription factors is involved in regulating macrophage polarization. At cellular level, although M1 and M2 macrophage activities exist without T or B cell influence, specialized or polarized T cells (Th1, Th2, Tregs) do play a role in macrophage polarized activation. Canonical IRF/STAT signaling is a central pathway in modulating macrophage polarization. Activation of IRF/STAT signaling pathways by IFNs and TLR signaling will skew macrophage function toward the M1 phenotype (via STAT1), while activation of IRF/STAT (via STAT6) signaling pathways by IL-4 and IL-13 will skew macrophage function toward the M2 phenotype. Signals initiated by IL-10, glucocorticoid hormones, apoptotic cell-released molecules, and immune complexes can also profoundly affect macrophage functional status. Macrophage polarization is also modulated by local microenvironmental conditions such as hypoxia. More importantly, M1-M2 polarization of macrophage is a highly dynamic process and the phenotype of polarized macrophages can be reversed under physiological and pathological conditions.

In step (a) of the method of the invention, the isolated macrophages are subjected to 1, 2, 3 or 4 consecutive series of hypoxia-reoxygenation. Thus, 5 or more hypoxia-reoxygenation series are excluded from the scope of the invention. Preferably, the step (a) of the method of the invention consists of 3 or 4 series of hypoxia-reoxygenation. More preferably, this step (a) consists of 4 series of hypoxia-reoxygenation. As shown in examples below, when macrophages are subjected to 4 hypoxia-reoxygenation series, a significantly higher overexpression of NGAL and IL-10 is achieved compared to control macrophages non-subjected to hypoxia-reoxygenation series or subjected to a different (lower or higher) number of hypoxia-reoxygenation series. Thus, this preferred embodiment wherein macrophages are subjected in step (a) to 4 hypoxia-reoxygenation series leads to improved macrophages with an improved M2 phenotype.

The overexpression of IL-10 and NGAL is important for tissue regeneration and anti-inflammatory activity of the resultant macrophages. "Interleukin 10 (IL-10)" is an anti-inflammatory cytokine with multiple, pleiotropic, effects in immunoregulation and inflammation. It downregulates the expression of Th1 cytokines, MHC class II antigens, and co-stimulatory molecules on macrophages. It also enhances B cell survival, proliferation, and antibody production. IL-10 is capable of inhibiting synthesis of pro-inflammatory cytokines such as IFN-γ, IL-2, IL-3, TNFα and GM-CSF made by cells such as macrophages and Th1 T cells. On the other hand, "NGAL" or "neutrophil gelatinase-associated lipocalin" is a 25-kDa protein of the lipocalin superfamily and exerts bacteriostatic effects by capturing and depleting siderophores. NGAL acts as a growth and differentiation factor in different cell types. Exogenous NGAL has been shown to cause expression of genetic markers reflecting early epithelial progenitors and to support proliferation of epithelial cells. NGAL also induces cell death in neutrophils and lymphocytes to limit inflammation, whereas nonhematopoietic cells and macrophages are resistant. Blocking NGAL production in macrophages reduces protective effects achieved with IL-10-overexpressing macrophages in a kidney ischemia/reperfusion injury model, substantiating NGAL-associated proproliferative and anti-inflammatory properties. NGAL overexpression in macrophages induces tissue regeneration prior to inflammation and reduces subsequent inflammation (levels of inflammatory cytokines are lowered and those of anti-inflammatory cytokines are increased). NGAL therefore presents proproliferative, proregenerative, and anti-inflammatory properties that make the resultant macrophages obtained by the method of the invention suitable for tissue regeneration/repair.

In the present invention, each "hypoxia-reoxygenation serie" comprises a first stage in which isolated macrophages are subjected to hypoxic conditions. This first stage is immediately followed by a second stage in which macrophages are subjected to standard oxygen conditions, i. e. in this second stage the oxygen concentration is restored in the cell environment. In a preferred embodiment, each serie of hypoxia-reoxygenation comprises between 2 and 5 minutes, more preferably 3 minutes, of hypoxia followed by at least 45 seconds of reoxygenation. More preferably, the reoxygenation stage is performed during no more than 1 minute.

"Hypoxic conditions" or "hypoxia conditions" are those in which cells are subjected to oxygen concentrations between 0 and 0.6%, preferably $O_2$ 0%. More preferably, the hypoxia is induced in a hypoxic chamber under the following conditions: nitrogen 95%; $CO_2$ 5%; $O_2$ 0%.

"Standard oxygen conditions" or "reoxygenation conditions" are those in which cells are subjected to atmospheric air. Preferably, the reoxygenation conditions are $CO_2$ 5% plus atmospheric air.

In the method described in the present invention, the hypoxia-reoxygenation series are performed continuously and consecutively in step (a), this means that no period of time exists between one serie and the following, but the reoxygenation stage of a previous serie is immediately followed by the hypoxia stage of the next serie.

In another preferred embodiment, the method of the invention comprises an additional step (a'), between the steps (a) and (b), which comprises subjecting the macrophages obtained after step (a) to a final reoxygenation step. That is, after the last hypoxia-reoxygenation serie an additional step consisting of a final reoxygenation stage may be optionally performed. This final reoxygenation step is carried out under standard oxygen conditions. In a more preferred embodiment, this final reoxygenation step is performed during no more than 1 hour and 30 minutes. In an even more preferred embodiment, this final reoxygenation step is performed during 1 h and 30 minutes.

The method of the invention may additionally comprise other steps such as, but without limitation, the maintenance and growth of macrophages under standard culture conditions before step (a), preferably during at least 24 h, and/or the maintenance and growth of the resultant macrophages under standard conditions after step (b), preferably during at least 1 h and 30 min.

The resultant macrophages obtained at the end of the method of the invention have a typical M2 phenotype;

however, it is known in the art that gene expression profiles and consequently functions of macrophages can differ based on the nature of the inductor stimulus. Thus, since the method of the invention comprises specific hypoxia-reoxygenation conditions that affect the macrophages polarization by altering and triggering specific signaling pathways, it is evident that those specific M2 macrophages obtained by the method of the invention are different in terms of gene expression profiles, and therefore in terms of functionality, from other M2 macrophages polarized or activated by other stimuli or by other hypoxic conditions different from those specifically described herein.

Thus, another aspect of the invention refers to an M2 macrophage or a population of M2 macrophages obtained or obtainable by the method of the invention, wherein said M2 macrophage (and the M2 macrophages comprised in the population) overexpresses at least NGAL. Hereinafter, these will be also named "M2 macrophage of the invention" and "M2 macrophage population of the invention". In a preferred embodiment, the M2 macrophage of the invention or the M2 macrophage population of the invention also overexpresses IL10.

The term "overexpression" as used herein refers to a gene expression level, specifically to a NGAL and IL-10 gene expression level, that is higher, preferably significantly higher, than the gene expression level of the same/s gene/s in control macrophages non-subjected to hypoxia-reoxygenation (but cultured under standard conditions) or non-subjected to the same hypoxia-reoxygenation conditions as those used for the macrophage/s under study or to be assessed.

The "overexpression" referred to in the present invention may be at protein or mRNA level, preferably at mRNA level. Thus, the expression "gene expression level" may be understood herein as "protein expression level" or "mRNA expression level".

The gene expression level may be measured or determined in cells by, for instance but without limitation, PCR, RT-LCR, RT-PCR, qRT-PCR or any other method for the amplification of nucleic acids, DNA microarrays made with oligonucleotides deposited by any method, DNA microarrays made with in situ synthesized oligonucleotides, in situ hybridization using specific labeled probes, electrophoresis gels, membrane transfer and hybridization with an specific probe, RMN, incubation with an specific antibody in assays such as Western blot, immunoprecipitation, protein arrays, immunofluorescence, immunohistochemistry, ELISA or any other enzymatic method, by incubation with a specific ligand, chromatography, mass spectrometry, and the like.

Once the resultant M2 macrophages are recovered in the step (b) of the method of the invention, these may be administered to the individual, preferably in the damaged area, for tissue repair or they may be added to medical or pharmaceutical compositions for their use as a medicament in cell therapy in the regeneration of damaged or injured tissues. Therefore, another aspect of the invention refers to a pharmaceutical composition, hereinafter "the composition of the invention" or "the pharmaceutical composition of the invention", comprising the M2 macrophage of the invention or the M2 macrophage population of the invention.

The pharmaceutical composition of the invention may additionally comprise a pharmaceutically acceptable vehicle, excipient, adjuvant and/or other active ingredient.

The term "excipient" makes reference to a substance which aids the absorption of the elements of the composition of the invention, stabilises said elements, activates or helps to prepare the composition in the sense of giving it consistency. Therefore, excipients may have a bonding function for keeping the ingredients bonded together, such as for example in the case of starches, sugars or celluloses, a sweetening function, a dyeing function, a protective function for protecting the composition, such as for example to isolate it from the air and/or humidity, a filling function for filling a pill, capsule or any other form of presentation, such as for example in the case of dibasic calcium phosphate, a disintegrating function to facilitate the dissolution of the components and their absorption, not excluding any type of excipients not mentioned in this paragraph.

The "pharmaceutically acceptable vehicle", like the excipient, is a substance or combination of substances used in the composition to dilute any of the components comprised therein up to a certain volume or weight. The term "vehicle" refers to a solvent, coadjuvant, excipient or carrier with which the composition of the invention must be administered; obviously, said vehicle must be compatible with said composition and with the cells comprised in it. Pharmaceutically acceptable vehicles may be, but not limited to, solids, liquids, solvents or surfactants. Examples of vehicles may be, but not limited to, water, oils or surfactants, including those of petroleum, animal, vegetable or synthetic origin, such as for example, in the non-limiting sense, peanut oil, soybean oil, mineral oil, sesame seed oil, castor oil, polysorbates, sorbitan esters, ether sulfates, sulfates, betains, glucosides, maltosides, fatty alcohols, nonoxinoles, poloxamers, poliethylenes, polyethylenglycols, dextrose, glycerol, digitonin and similar. The pharmacologically acceptable vehicle is an inert substance or vehicle having an action similar to any of the elements comprised in the composition of the present invention. The function of the vehicle is to facilitate the incorporation of other elements, enable better dosing and administration or give consistency and format to the composition. When the format of the presentation is liquid, the pharmacologically acceptable vehicle is the solvent.

The composition of the invention comprises the M2 macrophages of the invention or the M2 macrophage population of the invention in a therapeutically effective amount or density. "Therapeutically effective amount" is understood to be the amount or density of M2 macrophages of the invention or the M2 macrophage population of the invention that, when administered to the patient to be treated, produces the desired effect, thereby promoting tissue repair and inflammation reduction. The therapeutically effective amount may vary depending on a variety of factors, for example, but not limited to, the type, severity and extension of the damage in the tissue, as well as age, physical condition, response or tolerance capacity to the cell therapy, etc., of the individual to whom the composition of the invention is going to be administered.

The composition of the invention and/or its formulations may be administered in a variety of ways including, but not limited to, parenteral, intraperitoneal, intravenous, intradermal, epidural, intraspinal, intrastromal, intraarticular, intrasinovial, intratecal, intralesional, intraarterial, intracardiac, intramuscular, intranasal, intracranial, cutaneous or subcutaneous, intraorbital, intracapsular, topic, ophthalmological or ocular, by means of surgical implant, internal surgical paint, infusion pump or via catheter.

The composition of the present invention can be formulated for administration to an animal, preferably a mammal, including humans, in a variety of ways known in the state of the art. Examples of preparations could include any solid composition (tablets, pills, capsules, bags, bottles, powders, granules, bars, pencils, vaporisers, aerosols, etc.), semi-solid (ointment, cream, balm, gel, hydrogel, foam, lotion, soap, gelatin, etc.) or liquid (aqueous or non-aqueous solutions, hydroalcoholic or hydroglycolic solutions, suspensions, emulsions, syrups, anhydrous compositions, aqueous dispersions, oils, milks, balsams, liniments, serums, etc.) for topic or parental administration, preferably parenteral administration. The composition of the present invention may also be in the form of sustained release formulations or any other conventional release system. The term "sustained release" is used in the conventional sense in reference to a compound or cell vehiculisation system that enables the gradual release of said cells during a period of time and preferably, although not necessarily, with relatively constant cell release over a period of time. Illustrative examples of sustained release vehicles or systems include, but are not limited to, liposomes, mixed liposomes, oleosomes, niosomes, etosomes, milicapsules, microcapsules, nanocapsules, sponges, cyclodextrins, blisters, micelles, mixed surfactant micelles, mixed surfactant phospholipid micelles, milispheres, microspheres, nanospheres, liposphere, microemulsions, nanoemulsions, miniparticles, miliparticles, microparticles, nanoparticles, solid lipid nanoparticles, nanostructured lipid media, polymer materials, biodegradable or non-biodegradable patches or implants, or biodegradable microparticles, such as for example biodegradable microspheres.

The composition of the present invention is also suitable for being applied by means of medical devices which make it possible to release the M2 macrophages of the invention or the M2 macrophage population of the invention in the desired area in adequate concentrations for tissue regeneration and/or reduction of tissue inflammation. These devices must be, preferably, appropriate for locally administering the cells, allowing the treatment to act on the affected region and not be dispersed. The devices can, for example, but not limited to, include the cells their interior or be coated therewith.

Another aspect of the invention refers to an implant (solid, liquid or semi-solid such as gel) or medical device comprising the M2 macrophages of the invention or the M2 macrophage population of the invention. This implant or medical device may comprise the macrophages in its interior or may be coated with them.

Another aspect of the invention refers to a medical device or medical instrument capable of isolating macrophages, preferably monocytes, from the individual, more preferably from the bloodstream, by means of for example a biocompatible gradient, wherein said medical device or instrument further comprises a chamber capable of inducing hypoxia conditions on the isolated cells. That is, the chamber (the hypoxia chamber) of this medical device is capable of subjecting the macrophages to hypoxia. Afterwards, macrophages subjected to hypoxia may be re-introduced in the body of the individual, preferably in the damaged tissue, for tissue repair or regeneration. Another aspect of the invention refers to the use of this medical device or instrument for the treatment of tissue damage, for tissue repair, tissue regeneration, tissue remodeling, wound healing, resolution of inflammation, treatment and/or repair of wounds, treatment of (tissue) inflammation, treatment of damaged, injured or impaired tissue and the like.

Thus another aspect of the present invention relates to a device which is capable of inducing hypoxia and re-oxygenation conditions on isolated cells. The proposed device allows implementing the method previously described.

The device comprises a removable chamber that, under aseptic conditions, can be filled with a biological sample, preferably a blood sample, or a cell fraction and can be further filled with at least two different gas compositions from at least two different gas sources. The device further allows the recovering of cells in a medical instrument suitable for the injection of the macrophages in a tissue.

The removable chamber of the device can also be used to centrifuge a biological sample, preferably blood, to obtain a plurality of cell fractions and to isolate a cell fraction from the biological sample.

Another aspect of the invention refers to the use of the M2 macrophage of the invention or the M2 macrophage population of the invention as a medicament, preferably a cell therapy medicament, more preferably in tissue repair, tissue regeneration, tissue remodeling, wound healing, resolution of inflammation, treatment and/or repair of wounds, treatment of (tissue) inflammation, treatment of damaged, injured or impaired tissue and the like.

Another aspect of the invention refers to the use of the M2 macrophage of the invention or the M2 macrophage population of the invention for the manufacture of a medicament, preferably wherein the medicament is a cell therapy medicament, more preferably for tissue repair, tissue regeneration, tissue remodeling, wound healing, resolution of inflammation, treatment and/or repair of wounds, treatment of (tissue) inflammation, treatment of damaged, injured or impaired tissue and the like.

Another aspect of the invention refers to a method for tissue repair, tissue regeneration, tissue remodeling, wound healing, resolution of inflammation, treatment and/or repair of wounds, treatment of (tissue) inflammation, treatment of damaged, injured or impaired tissue and the like, in a subject in need thereof that comprises administering to the subject a therapeutically effective amount of the M2 macrophages of the invention or the M2 macrophage population of the invention or the pharmaceutical composition of the invention.

Another aspect of the invention refers to the M2 macrophage of the invention or the M2 macrophage population of the invention for use as a medicament. In a preferred embodiment, the medicament is a cell therapy medicament.

As used herein "cell therapy" (also called "cellular therapy" or "cytotherapy") refers to the therapy in which cellular material or cells is injected into a patient; in the context of this invention this means intact, living cells.

Another aspect of the invention refers to the M2 macrophage of the invention or the M2 macrophage population of the invention for use in the treatment of tissue damage, or for use in tissue repair, tissue regeneration, tissue remodeling, wound healing, resolution of inflammation, treatment and/or repair of wounds, treatment of (tissue) inflammation, treatment of damaged, injured or impaired tissue and the like.

Preferably, the tissue to be repaired according to the present invention is skeletal muscle, skin, nervous tissue, kidney, liver, brain, lung or in general any swollen body tissue. More preferably, the tissue to be repaired is skeletal muscle, even more preferable skeletal muscle injured by overuse or trauma.

Another aspect of the invention refers to a kit, hereinafter "kit of the invention", comprising the M2 macrophages of the invention, the M2 macrophage population of the invention or the pharmaceutical composition of the invention, preferably in a therapeutically effective amount, and a medical instrument suitable for the injection of the macrophages in a tissue.

A "medical instrument suitable for the injection of the macrophages in a tissue" is any medical device or instrument that may be used for the inclusion (preferably injection) of cells in a body or tissue. Examples of these devices or instruments are, but without limitations, syringes, vials, catheters, needles, cannulas, or in general any instrument used in cell therapies of those known in the art.

The M2 macrophages of the invention, the M2 macrophage population of the invention or the pharmaceutical composition of the invention may be encapsulated, for instance in vials, labeled and/or immobilized in a support in the kit of the invention.

Additionally, the kit of the invention may comprise other elements useful for the in vitro or ex vivo maintenance of the M2 macrophages of the invention, the M2 macrophage population of the invention or the pharmaceutical composition of the invention in the kit.

The kit of the invention may also comprise elements that prevent the contamination of the M2 macrophages included in it, such as antibiotic, bacteriostatic, bactericidal and/or fungicidal compounds, and the like.

The kit of the invention may also comprise other compounds, pharmaceutical compositions or medicaments suitable for the treatment of tissue damage, for tissue repair, tissue regeneration, tissue remodeling, wound healing, resolution of inflammation, treatment and/or repair of wounds, treatment of (tissue) inflammation, treatment of damaged, injured or impaired tissue and the like. These additional compounds would act as adjuvants (in combination) in the cell therapy with the M2 macrophages of the invention, the M2 macrophage population of the invention or the pharmaceutical composition of the invention.

Another aspect of the invention refers to a method for the treatment of tissue damage, for tissue repair, tissue regeneration, tissue remodeling, wound healing, resolution of inflammation, treatment and/or repair of wounds, treatment of (tissue) inflammation or treatment of damaged, injured or impaired tissue, in a subject in need thereof wherein said method comprises the step of subjecting the injured tissue or the injured area to at least one but less than five, preferably to 2, 3, or 4, more preferably to 3 or 4, even more preferably to 4, series of hypoxia-reoxygentation. In a preferred embodiment of this method of the invention, each serie of hypoxia-reoxygenation comprises no more than 3 minutes of hypoxia followed by at least 45 seconds of reoxygenation. In another preferred embodiment of this method of the invention, it further comprises an additional step, after the hypoxia-reoxygenation protocol, comprising the external injection of isolated cells into the injured tissue, more preferably these isolated cells are M2 macrophages. Even more preferably, these M2 macrophages have been previously polarized to an M2 phenotype through the method for obtaining macrophages polarized to an M2 phenotype described above in the present invention as "the method of the invention". Alternatively, these M2 macrophages have been previously polarized to an M2 phenotype using a solution of IL10. In a more preferred embodiment of this aspect of the invention, these M2 macrophages have been previously polarized from autologous macrophages, even more preferably from autologous peritoneal macrophages.

The method explained in the paragraph above may be performed, for example but without limitation, by means of a blood occlusion device for inducing hypoxia. An example of this device is a sphygmomanometer but other devices suitable for blood occlusion known in the art could be alternatively used. An $O_2$ sensor could also be present in order to monitor the process. The $O_2$ sensor and the blood occlusion device may be fixed to the injured tissue or area, for example positioning the sensor caudally to the blood occlusion device and close to or in the lesion site. Pressure through the blood occlusion device should be applied in the injured tissue during no more than three minutes or until $O_2$ saturation is equal or lower to 40%. Then, the pressure is released during at least 45 seconds or until $O_2$ saturation is recovered to normal levels. This process is repeated between one and four times, preferably 2, 3, or 4 times, more preferably between 3 or 4 times, even more preferably 4 times.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings and sequence listing are provided by way of illustration and are not intended to be limiting of the present invention.

EXAMPLES

Example 1

Figure 1:
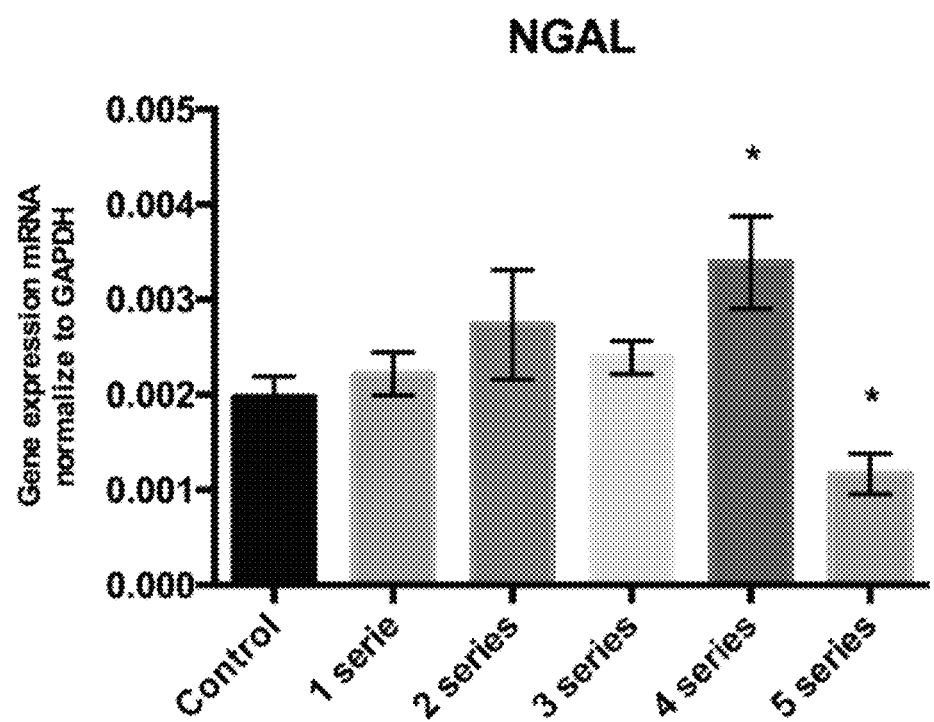
FIG. 1. NGAL gene expression (mRNA) normalize to GAPDH in macrophages in culture subjected to 1, 2, 3, 4 or 5 hypoxia-reoxygenation series or cultured under standard conditions (control). *P<0.005.

Effects of Short Periods of Anoxia-Reoxygenation on the Polarization of Peritoneal Macrophages 1.1. Objective.

The goal was to assess if the exposure of the macrophages to 1, 2, 3, 4 or 5 anoxia-reoxygenation series (3'anoxia-45" reoxygenation) promotes the polarization of macrophages to an M2 phenotype, with an increase in NGAL and IL10 expression compared to the control subjected to standard incubation conditions.

1.2. Experimental Design.

a. Control group under oxygen standard conditions ($CO_2$ 5% plus atmospheric air).

Peritoneal macrophages were extracted and isolated from six mice and cultured during 24 h under standard conditions.

b. Groups subjected to 1, 2, 3, 4 or 5 anoxia (nitrogen 95%; $CO_2$ 5%; $O_2$ 0%).-reoxygenation series plus 1 h and 30 min of reoxygenation.

Peritoneal macrophages were extracted and isolated from six mice and cultured during 24 h under standard conditions. Then, macrophages were subjected to 1, 2, 3, 4 or 5 anoxia-reoxygenation series (3'anoxia-45" reoxygenation). Finally, macrophages were subjected to 1 h and 30 min of reoxygenation.

1.3. Material and Methods.

For the extraction of peritoneal macrophages, 2.5 ml thioglycolate were intraperitoneally injected in 6 mice.

This process was performed 6 times, one for each mouse:

1. Peritoneal macrophages were extracted in 20 ml PBS.
2. Cells were resuspended in 1 ml RPMI medium 10% PBS 1% P/S (penicillin/streptomicin).
3. Cells were counted and 3.5 million per well of live cells were seeded (Table 1).

TABLE 1

| Mice | Million | % live cells | Million of live cells | µl of cells per well | Million/well |
|---|---|---|---|---|---|
| 1 | 64 | 60 | 38.4 | 91.14583333 | 3.5 |
| 2 | 39 | 55 | 21.45 | 163.1701632 | 3.5 |
| 3 | 72 | 66 | 47.52 | 73.65319865 | 3.5 |
| 4 | 30 | 66 | 19.8 | 176.7676768 | 3.5 |
| 5 | 31 | 60 | 18.6 | 188.172043 | 3.5 |
| 6 | 33 | 60 | 19.8 | 176.7676768 | 3.5 |

Cells were incubated under standard conditions during 24 h.

Afterwards, our intermittent anoxia protocol was performed in a hypoxia chamber under the following conditions: nitrogen 95% and $CO_2$ 5%, 0% $O_2$. Groups to be assessed were the following:

1. Control under oxygen standard conditions ($CO_2$ 5% plus atmospheric air). Peritoneal macrophages in a well containing 2 ml RPMI medium 10% FBS 1% P/S during 24 h.

2. 1 anoxia-reoxygenation serie. Peritoneal macrophages in a well containing 2 ml RPMI medium 10% FBS 1% P/S. 1 serie consisting of 3' anoxia/45" reoxygenation+1 h and 30 min of reoxygenation.

3. 2 anoxia-reoxygenation series. Peritoneal macrophages in a well containing 2 ml RPMI medium 10% FBS 1% P/S. 2 series consisting of 3' anoxia/45" reoxygenation+1 h and 30 min of reoxygenation.

4. 3 anoxia-reoxygenation series. Peritoneal macrophages in a well containing 2 ml RPMI medium 10% FBS 1% P/S. 3 series consisting of 3' anoxia/45" reoxygenation+1 h and 30 min of reoxygenation.

5. 4 anoxia-reoxygenation series. Peritoneal macrophages in a well containing 2 ml RPMI medium 10% FBS 1% P/S. 4 series consisting of 3' anoxia/45" reoxygenation+1 h and 30 min of reoxygenation.

6. 5 anoxia-reoxygenation series. Peritoneal macrophages in a well containing 2 ml RPMI medium 10% FBS 1% P/S. 5 series consisting of 3' anoxia/45" reoxygenation+1 h and 30 min reoxygenation.

Once each protocol ended in each group, cells were incubated under standard conditions during 1 h and 30 min. After this time, cells were harvested and frozen in dry pellet for the subsequent RNA extraction protocol.

RNA was extracted from the frozen samples and a reverse transcription to cDNA was carried out. Total RNA from cells was isolated using the RNeasy mini kit following the manufacturer's protocol (Qiagen, Barcelona, Spain). RNA concentrations were calculated from $A_{260}$ determinations using a Nanodrop ND-1000 (NanoDrop Technologies, Wilmington, Del., USA). cDNA was synthesized by using the iScript cDNA synthesis Kit from Bio-Rad according to the manufacturer's recommendations. Quantitative RT-PCRs were performed on a Bio-Rad iCycler iQ Real-Time-PCR detection system using SYBR Green RT-PCR detection Kit (Bio-Rad, Madrid, Spain) according to the manufacturer's instructions. Real-time PCR results were quantified using Gene Expression Macro (version 1.1) from Bio-Rad, with glyceraldehyde-3-phosphate dehydrogenase (GAPDH) as internal control for stable expression (housekeeping gene).

Several RT-PCRs were run in order to assess the NGAL and IL10 expression in each group.

1.4. Results.

Figure 2:
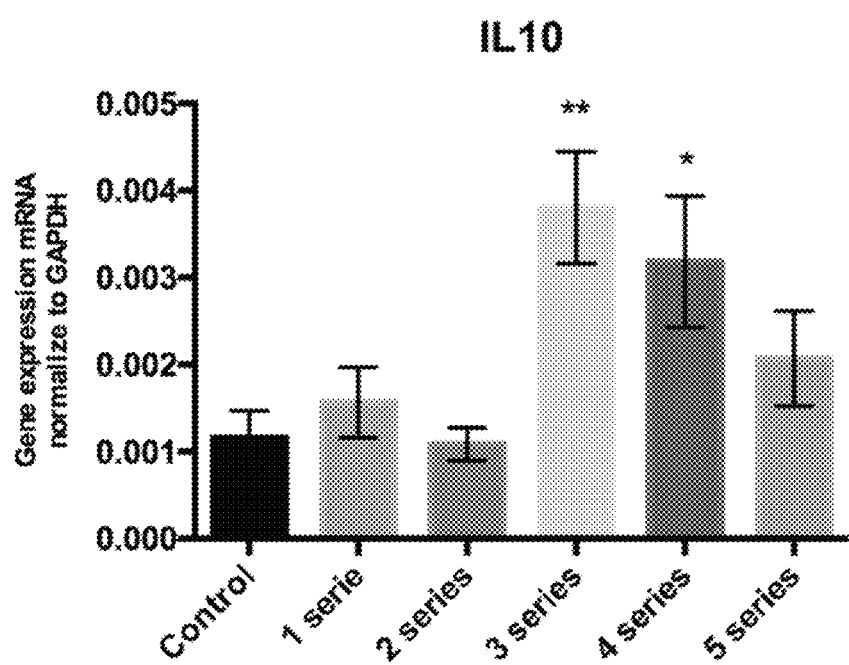
FIG. 2. IL10 gene expression (mRNA) normalize to GAPDH in macrophages in culture subjected to 1, 2, 3, 4 or 5 hypoxia-reoxygenation series or cultured under standard conditions (control). *P<0.005. **P<0.001.

Although 1, 2, and 3 series of 3' anoxia-45" reoxygenation also lead to an increased NGAL expression, significance in the both parameters measured (NGAL and IL-10) only was achieved with 4 series, whereas 5 series decreased NGAL levels (FIGS. 1 and 2).

Example 2

Description of a Preferred Embodiment of the Device

Figure 3A:
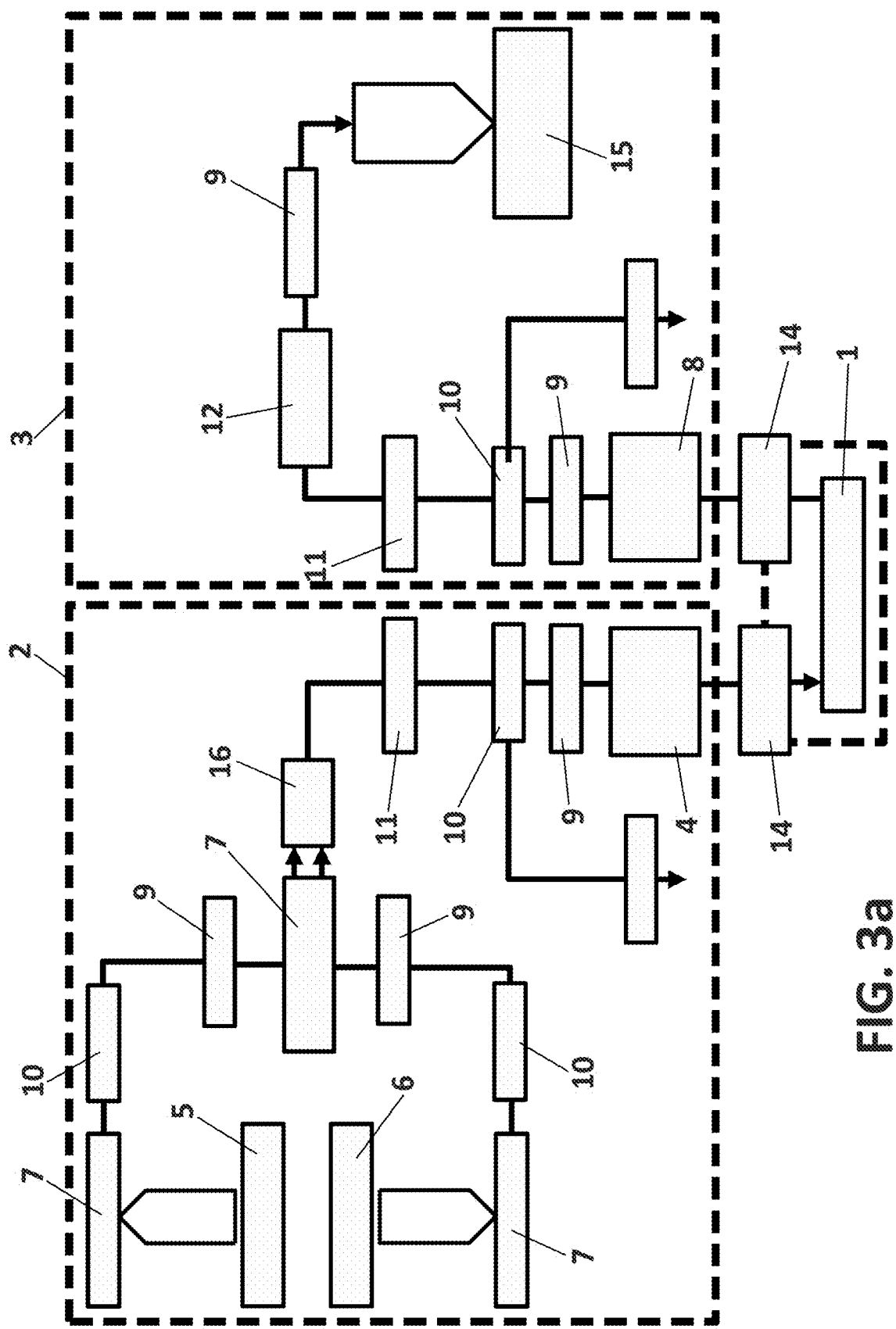
FIG. 3A. Shows a diagram of the device for inducing hypoxia and re-oxygenation conditions on isolated macrophages.
Figure 3B:
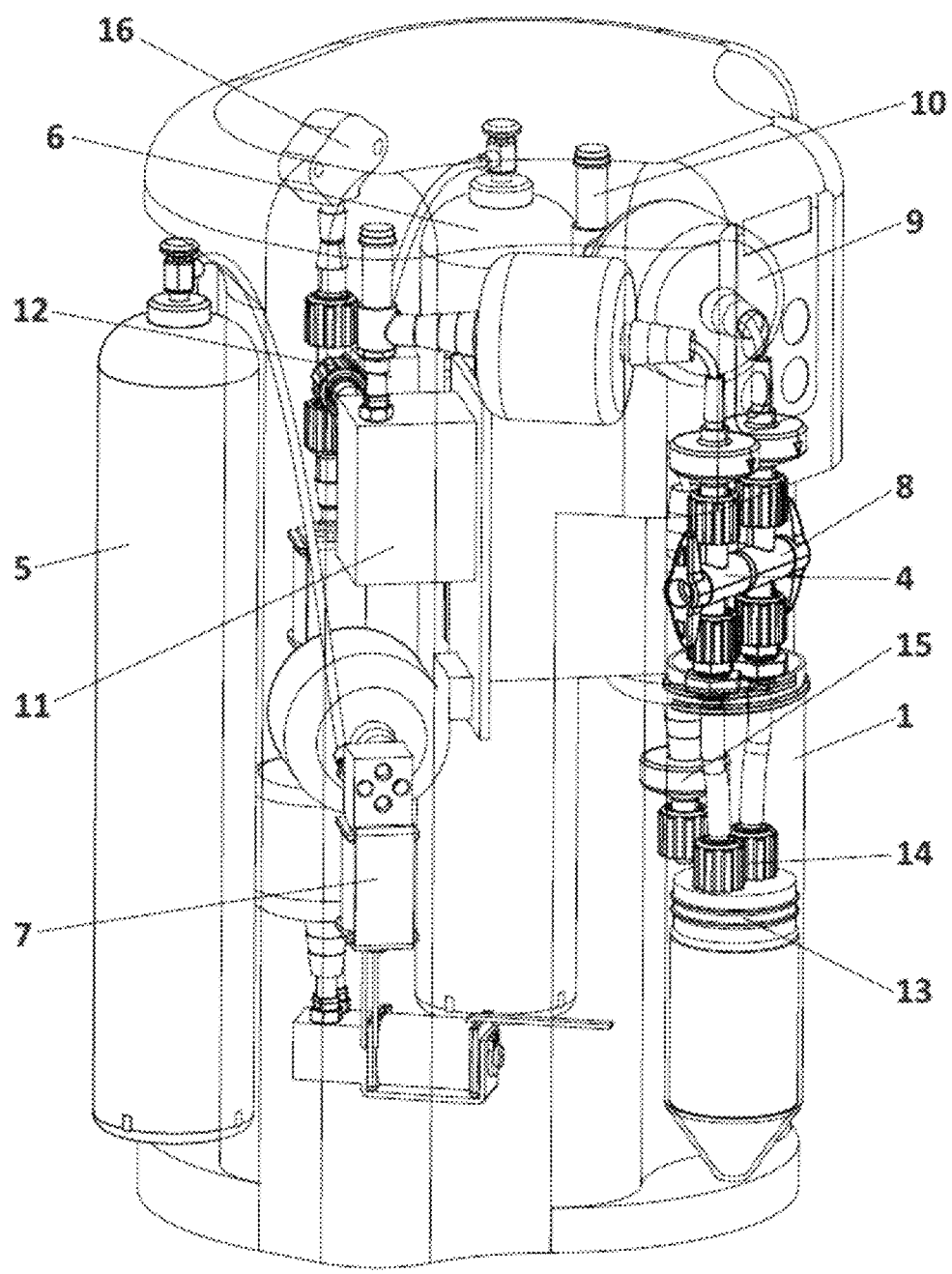
FIG. 3B. Shows a perspective view of the device for inducing hypoxia and re-oxygenation conditions on isolated macrophages.

In FIG. 3A it can be appreciated a diagram of the proposed device for inducing hypoxia and re-oxygenation conditions on isolated macrophages according to the method previously described. In FIG. 3B there is a perspective view of said device.

As can be seen in said figure, the essential elements of the device are a removable chamber (1) configured to house the isolated macrophages, a first gas conduction circuit (2) and a second gas conduction circuit (3).

The first gas conduction circuit (2) comprises a first removable connection (4), which is preferably a stopcock, to the removable chamber (1) and a first gas source (5) and a second gas source (6). The first and second gas sources (5, 6) are connected to an electrovalve (7) which is configured to select the gas source from which the gas passes to the removable chamber (1).

The first gas conduction circuit (2) can also comprise a press sensor (16) placed between the electrovalve (7) and the first removable connection (4). In other embodiments of the invention, the press sensor (16) is placed between the electrovalve (7) and the gas sensor (11) or safety valve (10) or HEPA filter (9).

The second gas conduction circuit (3) comprises a second removable connection (8) to the removable chamber (1) and a connection to the external environment (15) or a connection to a vacuum device. The second gas conduction circuit (3) is configured to control the removal of a gas inside the interior of the removable chamber (1).

The first gas conduction circuit (2) further comprises at least one HEPA filter (9) and/or safety valve (10) between the first gas source (5) and the valve (7) or between the second gas source (6) and the valve (7). Preferably, when the device comprises both elements, the safety valve (10) is placed between the first gas source (5) or the second gas source (6) and the valve (7).

In this case, the safety valve (10) is meant to protect the first gas conduction circuit (2) against over pressures. That is the reason why it has to be placed in the inlets and outlets of the first gas conduction circuit (2).

The device can also comprise, in the first gas conduction circuit (2), a gas sensor (11) placed between the valve (9) and the first removable connection (4) to the removable chamber (1). Since there is no possible to introduce gas sensors in the interior of the removable chamber (1), in order to assure the quantity of gas to be introduced, in a preferable embodiment of the invention there is a gas sensor (11) in the inlet/outlet of the gas from said removable chamber (1).

Preferably, the first gas conduction circuit (2) further comprises a safety valve (10) and/or an HEPA filter (9) between the gas sensor and the first removable connection (4).

The first removable connection (4) is preferably a luer-lock connector or a luer-lock valve.

Additionally, the second gas conduction circuit (3) can comprise at least an HEPA filter (9) and/or a safety valve (10) between the second removable connection (8) and the a connection to the external environment (15) or the connection to a vacuum device. In cases in which both elements are present, the HEPA filter (9) is placed, preferably, between the second removable connection (8) and the safety valve (10).

The second removable connection (8) is preferably a luer-lock connector or a luer-lock valve.

In the second conduction circuit (3), the safety valve (10) is meant to protect said gas conduction circuit (3) against over pressures.

The first removable connection (4) and the second removable connection (8) are configured to be connected to at least a reception connection (14) of the removable chamber (1). The at least one reception connection (14) is, in an embodiment of the invention, a stop lock with a luer-lock valve.

The second gas conduction circuit (3) can also comprise a gas sensor (11) between the second removable connection (8) and the connection to the external environment (15) or the connection to a vacuum device.

Also the second gas conduction circuit (3) can comprise at least an electrovalve and/or a pump (12) between the second removable connection (8) and the connection to a vacuum device or the connection to the external environment (15).

Preferably, the removable chamber (1) is a centrifuge tube. In FIGS. 4a-d some different embodiments of the removable chamber (1) are shown. The device can also comprise a controller configured for receiving signals from the gas sensors (11) and, in accordance with the received signals, control the valve (7) and the electrovalve or pump (12) in order to select from which gas source (5, 6) fill the removable chamber (1).

Figure 4A:
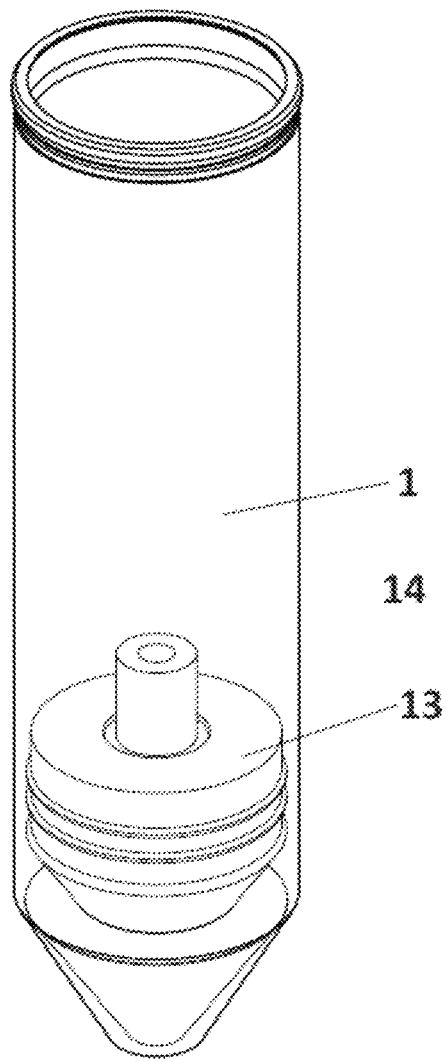
FIGS. 4A-D. Show different embodiments of the removable chamber of the device of FIGS. 3A-B.
Figure 4B:
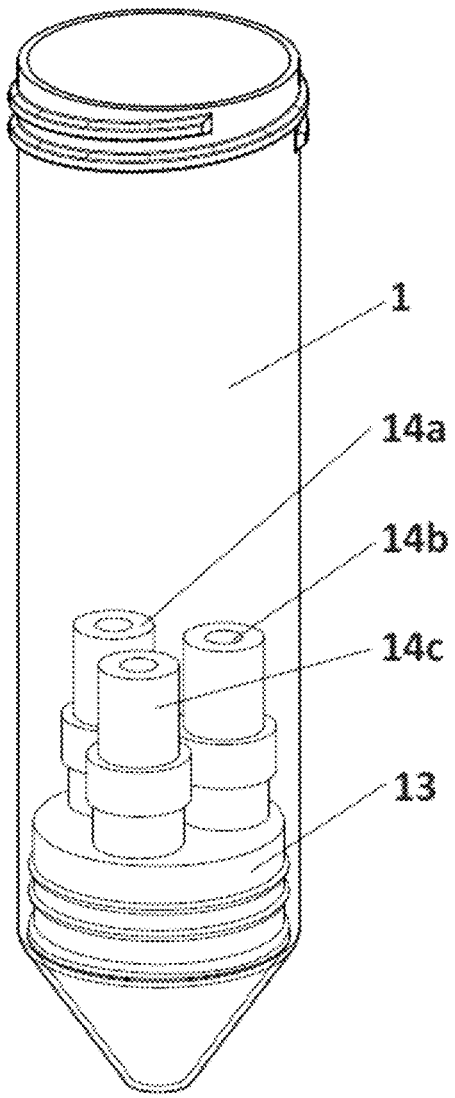

As previously described, the removable chamber (1) is preferably a tube and more preferably a centrifuge tube. It can comprise a plunger (13) which can be moved longitudinally through the chamber and said plunger (13) comprises, as seen in FIG. 4A, at least one port with one reception connection (14), preferably a luer-lock valve which can be coupled to a syringe or to any other suitable device to introduce or remove the cells from inside the removable chamber (1). Afterwards, the reception connection (14) can be hermetically coupled to the first and second gas conduction circuits (5, 6) to fill and remove gas from inside the removable chamber (1).

In a particular embodiment (FIG. 4B), the plunger (13) comprises a common reception connection for inlet and outlet of a gas which can be connected to a syringe, a second reception connection (14b) that can be hermetically coupled to the first gas conduction circuit (2) and a third reception connection (14c) that can be hermetically coupled to the second gas conduction circuit (3).

Figure 4C:
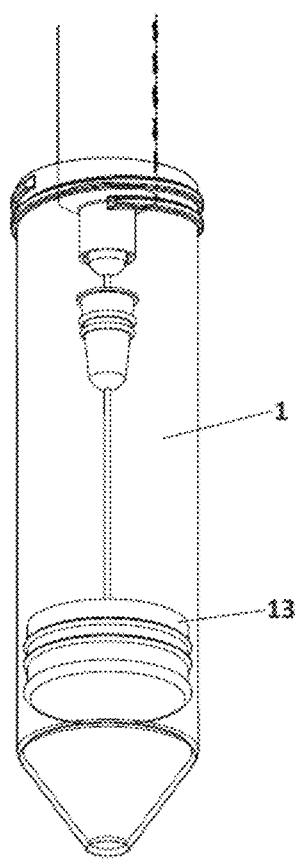
Figure 4D:
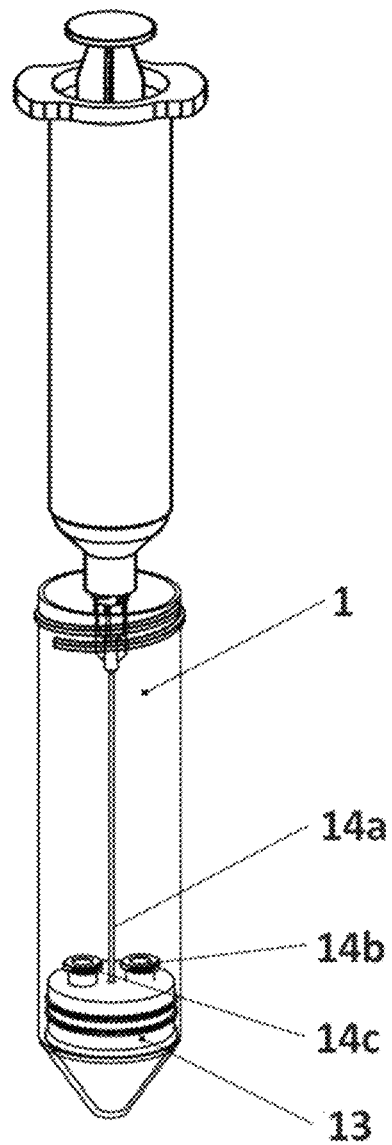
Figure 5:
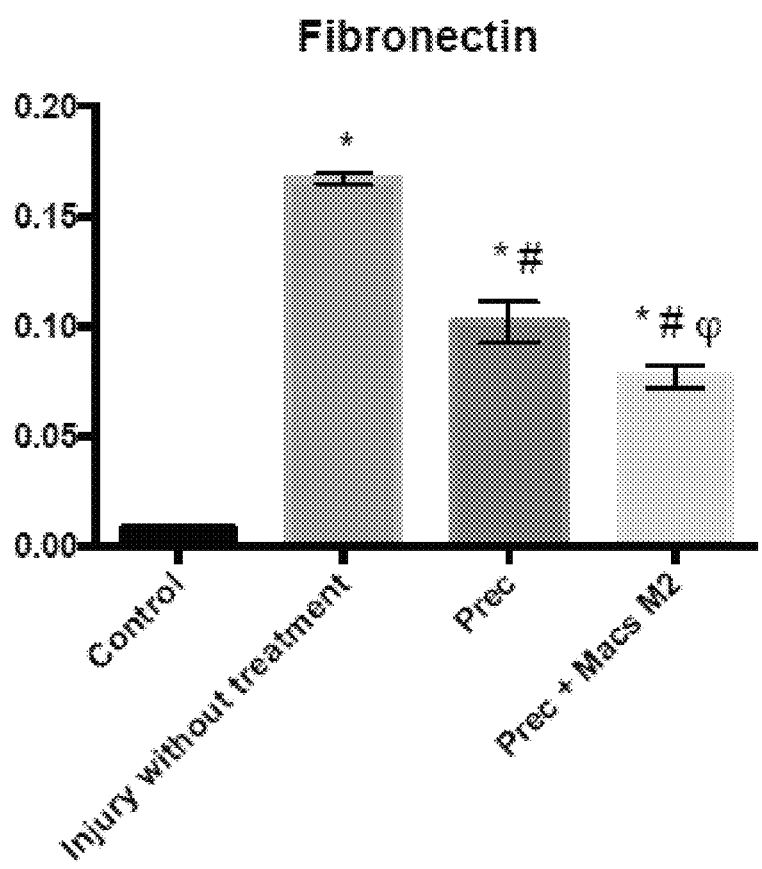
FIG. 5. Expression of fibronectin (mRNA) normalize to GAPDH in the muscle collected from mice. PREC: mice with injury treated with the in vivo hypoxia-reoxygentation protocol. PREC+Macs M2: mice with injury treated with the in vivo hypoxia-reoxygentation protocol+M2 macrophages.
Figure 6:
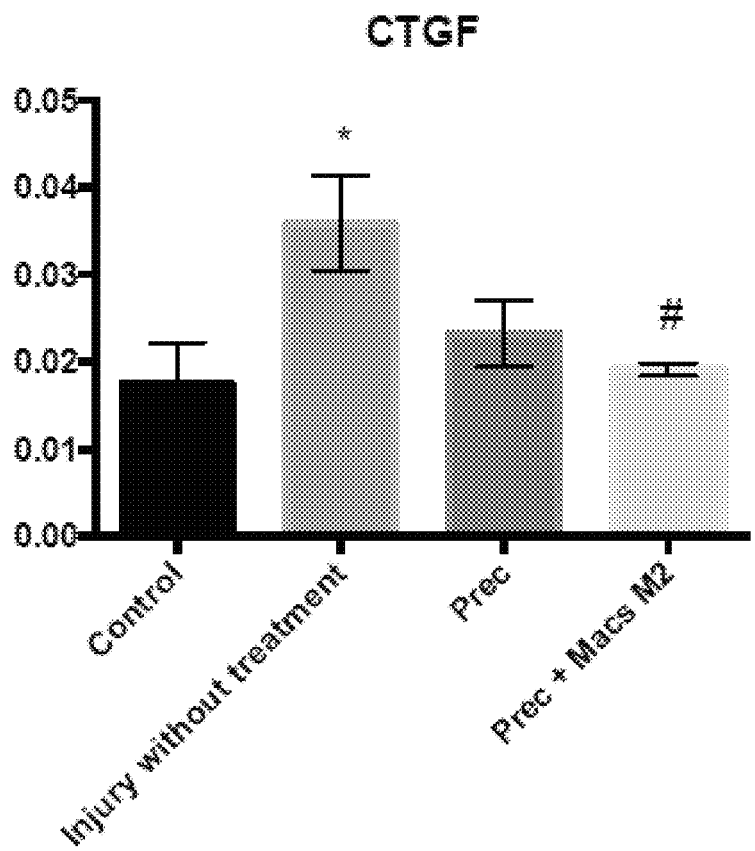
FIG. 6. Expression of connective tissue grow factor (CTGF) (mRNA) normalize to GAPDH in the muscle collected from mice. PREC: mice with injury treated with the in vivo hypoxia-reoxygentation protocol. PREC+Macs M2: mice with injury treated with the in vivo hypoxia-reoxygentation protocol+M2 macrophages.
Figure 7:
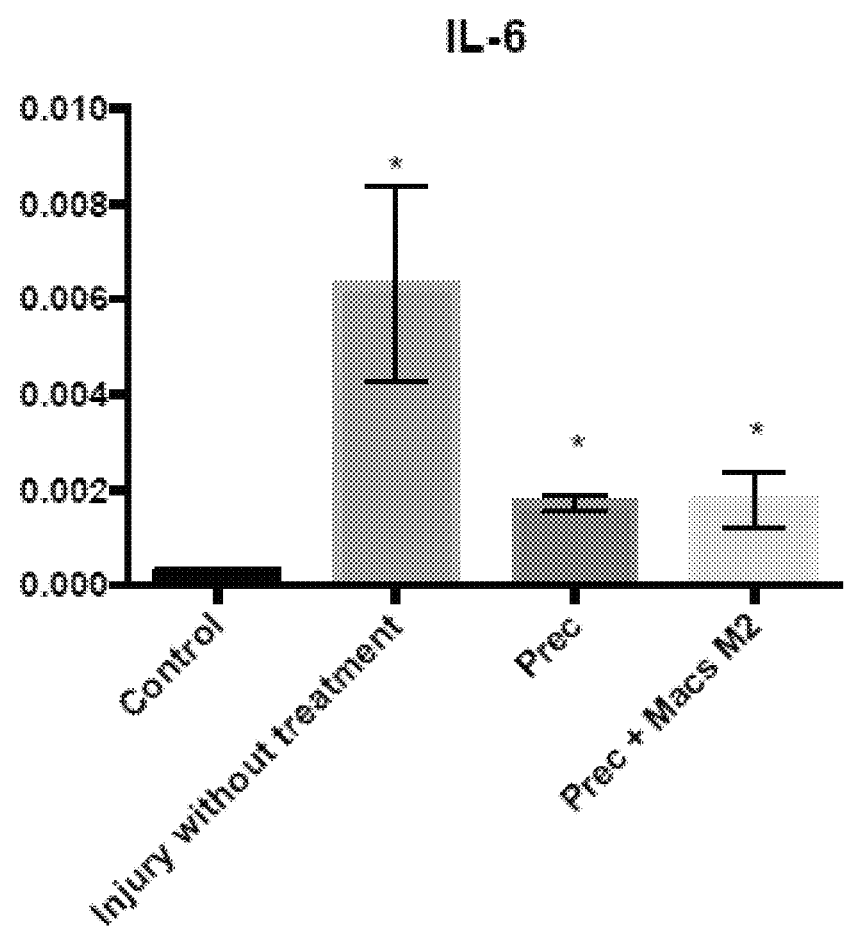
FIG. 7. Expression of IL-6 (mRNA) normalize to GAPDH in the muscle collected from mice. PREC: mice with injury treated with the in vivo hypoxia-reoxygentation protocol. PREC+Macs M2: mice with injury treated with the in vivo hypoxia-reoxygenation protocol+M2 macrophages.
Figure 8:
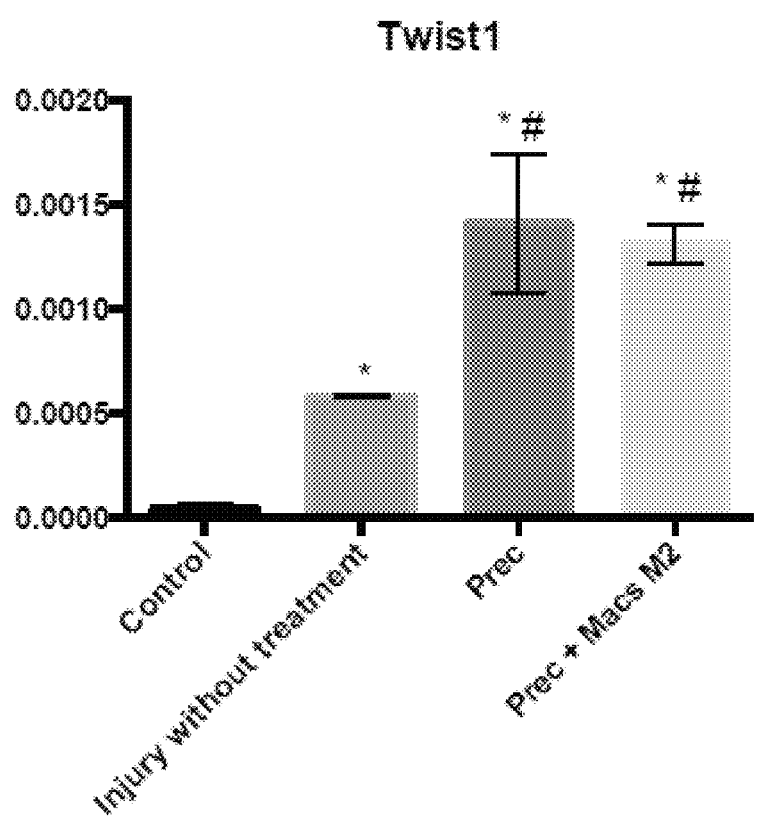
FIG. 8. Expression of TWIST1 (mRNA) normalize to GAPDH in the muscle collected from mice. PREC: mice with injury treated with the in vivo hypoxia-reoxygentation protocol. PREC+Macs M2: mice with injury treated with the in vivo hypoxia-reoxygentation protocol+M2 macrophages.

In another possible embodiment, as shown in FIG. 4C, the plunger (13) can be punched with a needle to introduce or remove the cells from inside the removable chamber (1) or to fill and remove a gas composition inside the removable chamber (1).

In another embodiment (FIG. 4D), the plunger (13) can be punched with a needle (14a) to introduce or remove the cells from inside the removable chamber (1) and comprises a first reception connection (14b) that can be hermetically coupled to the first gas conduction circuit (2) and a second reception connection (14c) that can be hermetically coupled to the second gas conduction circuit (3).

A description is made of an example process carried out in the device. In this case, a blood sample from an individual is introduced, using a syringe, in a tube (the removable chamber (1)) and submitted to centrifugation in order to obtain a plurality of cell fractions. Afterwards, a second syringe is connected to the reception connection (14) (luer-lock) of the removable chamber (1) and, moving the plunger (13) downwards through the removable chamber (1), the syringe is filled with an isolated cell fraction. This process can be repeated several times until the cell fraction of interest is separated in an individual syringe.

The cell fraction of interest is introduced in a removable chamber (1) of the device. This removable chamber (1) is connected to the device and is first filled with a first gas composition ($N_2$) displacing the previous gas composition inside the removable chamber (1) through the second gas conduction circuit (3), and later filled with a second gas composition (synthetic air) displacing the first gas composition inside the removable chamber (1) through the second gas conduction circuit (3). This process is repeated four times.

The removable chamber (1) is disconnected from the device, a syringe is connected to the reception connection (14) and, moving the plunger (13) downwards through the removable chamber (1), the cell fraction is recovered in the syringe.

Example 3

In Vivo Therapy for Treating Injured Tissue 3.1. Experimental Design and Procedure.
 a. Mice without injury (Control)
 b. Mice with an injury not treated
 c. Mice with an injury treated with an in vivo ischemia reperfusion protocol (PREC)
 d. Mice with an injury treated with an in vivo ischemia reperfusion protocol (PREC)+M2 macrophages An injury in the mice leg muscle was performed by laceration using a 5 mm diameter biopsy.
After 48 h Peritoneal macrophages were extracted and isolated from mice (d) and polarized to an M2 phenotype using the procedure described in example 1.

The legs of mice (c) and (d) were surrounded with a plastic track above the twin. Once it is well caught, it begins to tighten to make it a restriction of the flow during 3 minutes. After this period the track is released and the blood flow was recovered during 45 seconds. Afterwards the same ischemia reperfusion process was repeated 2 times.

After the PREC protocol, M2 macrophages were injected to mice (d).
After 96 hours The animals were sacrificed. Once the muscle was collected, it was cut in two parts and inserted in dry ice. Subsequently, the tissue was frozen at −80° and the RNA was extracted from a single piece using trizol. Due to the high values of RNA obtained in tissue, it was diluted in half with RNAse free water, the CDNA was made and the expression of the following genes was quantified:

FIBRONECTIN (FIG. 5)
CTGF (FIG. 6)
IL-6 (FIG. 7)
TWIST 1 (FIG. 8)

The fibronectin, "connective tissue grow factor" (CTGF) and IL-6 markers were significantly reduced in the groups of animals receiving the treatment, indicating that the therapy is capable of reducing markers of fibrosis and inflammation. The increase of Twist1 marker also indicates that the treatment favors cell proliferation. The in vivo therapy described herein is therefore useful in the amelioration of inflammation and scar formation and for tissue remodeling.

The invention claimed is:

1. An in vitro method for obtaining macrophages polarized to an M2 phenotype that comprises:
 a. subjecting isolated macrophages to 4 series of hypoxia-reoxygenation, and
 b. recovering the macrophages obtained after step (a), wherein the macrophages recovered after step (b) overexpress NGAL and IL10.

2. The method according to claim 1, wherein each series of hypoxia-reoxygenation comprises between 2 and 5 minutes of hypoxia followed by at least 45 seconds of reoxygenation.

3. The method according to claim 1, which comprises an additional step (a'), between the steps (a) and (b), comprising subjecting the macrophages obtained after step (a) to a final reoxygenation step.

4. The method according to claim 3, wherein the final reoxygenation step is performed during no more than 1 hour and 30 minutes.

5. The method according to claim 1, wherein the macrophages of step (a) are monocytes.

* * * * *